(12) United States Patent
Ikeda

(10) Patent No.: US 6,933,310 B1
(45) Date of Patent: Aug. 23, 2005

(54) THERAPEUTIC AGENT FOR AMYOTROPHIC LATERAL SCLEROSIS (ALS)

(75) Inventor: Ken Ikeda, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/399,961

(22) PCT Filed: Nov. 13, 2000

(86) PCT No.: PCT/JP00/07994

§ 371 (c)(1),
(2), (4) Date: Aug. 26, 2003

(87) PCT Pub. No.: WO02/34264

PCT Pub. Date: May 2, 2002

(30) Foreign Application Priority Data

Oct. 24, 2000 (JP) .............................. 2000-324476

(51) Int. Cl.[7] .......................................... A61K 31/415
(52) U.S. Cl. ...................... 514/403; 424/400; 424/451; 424/464; 424/489
(58) Field of Search ...................... 514/403; 424/400, 424/451, 464, 489

(56) References Cited

U.S. PATENT DOCUMENTS

| | | | |
|---|---|---|---|
| 4,857,542 A | 8/1989 | Nishi et al. | 514/404 |
| 5,527,814 A | 6/1996 | Louvel | 514/367 |
| RE35,801 E | 5/1998 | Nishi et al. | 514/404 |
| 2002/0198172 A1 * | 12/2002 | Sandage et al. | 514/49 |

FOREIGN PATENT DOCUMENTS

| | | |
|---|---|---|
| EP | 208874 | 1/1987 |
| EP | 558861 | 9/1993 |
| EP | 0 633 025 | 1/1995 |
| JP | 5-35128 | 5/1987 |
| JP | 3-215425 | 9/1991 |
| JP | 3-215426 | 9/1991 |
| JP | 5-31523 | 5/1993 |
| JP | 7-25765 | 1/1995 |
| JP | 7-121861 | 12/1995 |
| JP | 9-52801 | 2/1997 |
| JP | 9-52831 | 2/1997 |
| JP | 63-132833 | 6/1998 |
| JP | 10-279480 | 10/1998 |
| JP | 11-79991 | 3/1999 |
| JP | 2906513 | 4/1999 |

OTHER PUBLICATIONS

CAS Registry entry for MCI 186.*
H. Kawai et al., "Effects of a Novel Free Radical Scavenger, MCI-186, on Ischemic Brain Damage in the Rat Distal Middle Celebral Artery Occlusion Model", The Journal of Pharmacology and Experimental Therapeutics, vol. 281, No. 2, issued 1997, pp. 921-927.

(Continued)

Primary Examiner—Gollamudi S. Kishore
Assistant Examiner—Simon J. Oh
(74) Attorney, Agent, or Firm—Wenderoth, Lind & Ponack, L.L.P.

(57) ABSTRACT

An object of the present invention is to provide a novel medicament with which motor neuron diseases can be treated. According to the present invention, there is provided a therapeutic agent for motor neuron diseases which comprises 3-methyl-1-phenyl-2-pirazoline-5-on or physiologically acceptable salts thereof as an active ingredient.

5 Claims, 4 Drawing Sheets

OTHER PUBLICATIONS

H. Mitsumoto et al., "Arrest of Motor Neuron Disease in Wobbler Mice Cotreated with CNTF and BDNF", Science, vol. 265, No. 5175, issued Aug. 1994, pp. 1107-1110.

Yamamoto et al.: "Delayed neuronal death prevented by inhibition of increased hydroxyl radical formation in a transient cerebral ischemia," Brain Research, vol. 762, No. 1-2, pp. 240-242, (1997) XP-002278046.

K. Kinoshita et al., "Feature: A new treatment for amyotrophic lateral sclerosis (ALS)", Cranial Nerves, vol. 50, No. 7, pp. 615-624, 1998 with English translation.

K. Ikeda et al., "Brain-derived neurotrophic factor attenuates neuromuscular dysfunction in wobbler mouse motor neuron disease", Ann. Neurol., 34, 304, 1993.

H. Mitsumoto et al., "The effects of ciliary neurotrophic factor on motor dysfunction in wobbler mouse motor neuron disease", Ann. Neurol., vol. 36, No. 2, pp. 142-148, Aug. 1994.

H. Mitsumoto et al., "Arrest of motor neuron disease in wobbler mice cotreated with CNTF and BDNF", Science, vol. 265, pp. 1107-1110, Aug. 1994.

\* cited by examiner before drug administration    2 weeks after administration    4 weeks after administration

THERAPEUTIC AGENT FOR AMYOTROPHIC LATERAL SCLEROSIS (ALS)

This application is a U.S. national stage of International Application No. PCT/JP00/07994 filed Nov. 13, 2000.

TECHNICAL FIELD

The present invention relates to a therapeutic agent for motor neuron diseases and an enhancing agent for motor neurons. More specifically, the present invention relates to a therapeutic agent for motor neuron diseases and an enhancing agent for motor neurons, which comprises 3-methyl-1-phenyl-2-pirazoline-5-on or physiologically acceptable salts thereof as an active ingredient.

BACKGROUND ART

Motor neuron diseases include amyotrophic lateral sclerosis (ALS) in which both primary motor neurons and secondary motor neurons are damaged, and spinal muscle atrophy (SMA) in which only secondary motor neurons are damaged, and other diseases are known such as progressive bulbar palsy, primary lateral sclerosis (PLS), and arthrogryposis multiplex congenita (AMC). Of these, ALS often begins in late middle age, and is a lethal intractable disease, in which the condition rapidly deteriorates from muscular atrophy and muscle weakness to, finally, death due to respiratory insufficiency or the like in a matter of a few years. The cause and pathology of ALS have not been sufficiently elucidated.

Major causes of ALS that have been proposed as hypotheses are: (1) autoimmunity (the appearance of autoantibody against Ca channels), (2) excitatory amino acid excess/toxicity (increased extracellular glutamic acid and blocked transport of glutamic acid), (3) oxidative stress disorders (neuronopathy due to abnormality of Cu/Zn superoxide dismutase (SOD) gene and free radical), (4) cytoskeletal disorders (accumulation of neurofilaments in motor nerve cells and appearance of inclusions), and (5) deficiency of neurotrophic factors, and the like.

Among these hypothesized causes of ALS, based on the oxidative stress disorder hypothesis, whether or not antioxidants are effective against ALS has attracted attention. For example, a lecithinized SOD therapy had been attempted (Cranial Nerves 50(7): 615–624, 1998). However, it was shown that even when human recombinant Cu/Zn SOD was administered intraspinally to ALS patients, effective therapeutic effects were not obtained (Cranial Nerves 50(7): 615–624, 1998).

Further, riluzole (JP Patent Publication (PCT Translation) No. 7-504655) (trade name: Rilutek (Rhone-poulenc Rorer)) is known as an existing therapeutic agent for ALS. This therapeutic agent is a benzothiazole compound, which has been shown to suppress glutamic acid transmission in glutaminergic nerves, and have a neuroprotective effect against neurodegeneration. Clinical trials of this therapeutic agent against ALS are underway, and the agent has been approved as a medicament. However, some test results have been reported in which effectiveness against ALS could not be confirmed. The development of a more effective therapeutic agent for ALS has been desired.

DISCLOSURE OF THE INVENTION

An object of the present invention is to provide a novel medicament with which motor neuron disease can be treated. More specifically, an object of the present invention is to provide a novel medicament, with which the progress of motor neuron diseases, such as amyotrophic lateral sclerosis (ALS), spinal muscle atrophy (SMA), progressive bulbar palsy, primary lateral sclerosis (PLS), or arthrogryposis multiplex congenita (AMC), can be delayed or their symptoms can be alleviated.

As a result of concentrated efforts to solve the above problems, the present inventor has found that when 3-methyl-1-phenyl-2-pirazoline-5-on was administered to motor neuron disease model animals [Wobbler mouse (Ikeda K. et al., Ann. Neurol. vol. 34, p304 (1993); Mitsumoto H. et al., Ann. Neurol. vol. 36, pp 142–148 (1994); Mitsumoto H. et al., Science, vol. 265, pp 1107–1110 (1994))], the progress of the forelimb muscle contracture and muscle weakness were delayed, and the weight of brachial biceps muscle, the mean diameter of muscle fiber, and the number of motor neurons were increased, as compared to a control group. The present invention has been completed based on these findings.

That is, according to the present invention, there is provided a therapeutic agent for motor neuron diseases which comprises 3-methyl-1-phenyl-2-pirazoline-5-on or physiologically acceptable salts thereof as an active ingredient. In a preferred embodiment of the present invention, the therapeutic agent of the present invention is used for delaying the progress of motor neuron diseases.

According to another aspect of the present invention, there is provided an enhancing agent for motor neurons which comprises 3-methyl-1-phenyl-2-pirazoline-5-on or physiologically acceptable salts thereof as an active ingredient.

According to further another aspect of the present invention, there is provided a method for treating motor neuron diseases which comprises the step of administering an effective amount of 3-methyl-1-phenyl-2-pirazoline-5-on or physiologically acceptable salts thereof to a patient. In a preferred embodiment of the present invention, the treatment method of the present invention delays the progress of motor neuron diseases.

According to further another aspect of the present invention, there is provided a method for enhancing motor neurons which comprises the step of administering an effective amount of 3-methyl-1-phenyl-2-pirazoline-5-on or physiologically acceptable salts thereof to a patient.

According to further another aspect of the present invention, there is provided a use of 3-methyl-1-phenyl-2-pirazoline-5-on or physiologically acceptable salts thereof for the production of the therapeutic agent for motor neuron diseases. In a preferred embodiment of the present invention, the therapeutic agent for motor neuron diseases is a therapeutic agent which delays the progress of motor neuron diseases.

According to further another aspect of the present invention, there is provided a use of 3-methyl-1-phenyl-2-pirazoline-5-on or physiologically acceptable salts thereof for the production of an enhancing agent for motor neurons.

In the present invention, the motor neuron disease is preferably amyotrophic lateral sclerosis (ALS), spinal muscle atrophy (SMA), progressive bulbar palsy, primary lateral sclerosis (PLS), or arthrogryposis multiplex congenita (AMC), and is particularly preferably amyotrophic lateral sclerosis (ALS).

BEST MODE FOR CARRYING OUT THE INVENTION

Figure 1:
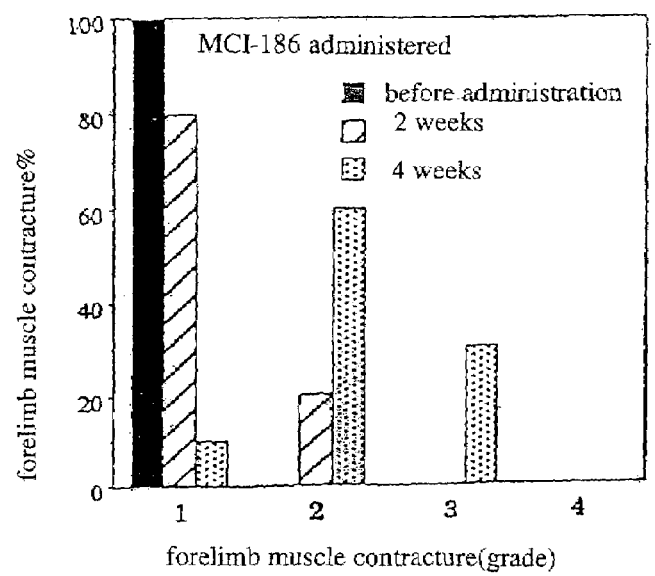
FIG. 1 shows the results of evaluating the degrees of forelimb muscle contracture as classified into Grades 1 to 4. The upper graph shows the results of a group administered with the medicament of the present invention, and the lower 3 graphs show the results of control groups.
Figure 1:
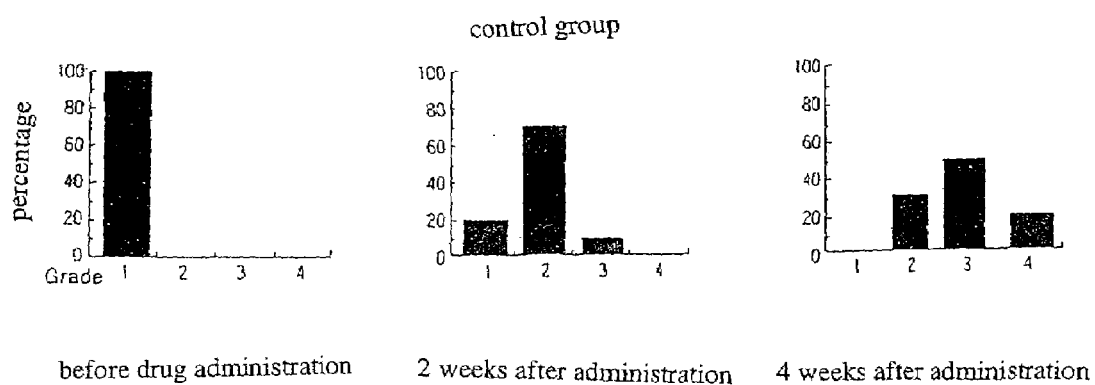

The medicament of the present invention is characterized in that it comprises 3-methyl-1-phenyl-2-pirazoline-5-on or physiologically acceptable salts thereof as an active ingredient, and is used as a therapeutic agent for motor neuron diseases or as an enhancing agent for motor neurons.

3-methyl-1-phenyl-2-pirazoline-5-on, which is used as an active ingredient in the medicament of the present invention, is one type of free radical scavenger that suppresses lipid hyperoxidation. 3-methyl-1-phenyl-2-pirazoline-5-on can be produced by, for example, a synthesis method as described in Section 7 of the JP Patent Publication (Examined Application) No. 5-31523. Known applications of the above compound as a medicament include cerebral function-normalizing action (JP Patent Publication (Examined Application) No. 5-31523), suppressive action on production of lipid peroxidate (JP Patent Publication (Examined Application) No. 5-35128, Compound in Example 1), antiulcer action (JP Patent Publication (Unexamined Application) No. 3-215425), suppressive action on hyperglycemic action (JP Patent Publication (Unexamined Application) No. 3-215426), eye disease suppressive action (JP Patent Publication (Unexamined Application) No. 7-25765), therapeutic and prophylactic action on acute renal failure (JP Patent Publication (Unexamined Application) No. 9-52831), preservative action on transplanted organs (JP Patent Publication (Unexamined Application) No. 9-52801), prophylactic and therapeutic action on damaged dermal tissue (JP Patent Publication (Unexamined Application) No. 10-279480), and prophylactic action on necrosis of transplanted skin or transplanted tissues (JP Patent Publication (Unexamined Application) No. 11-79991). However, each of these publications neither suggests nor teaches the action of the above compounds against motor neuron diseases.

In addition to the above compounds in free forms, physiologically acceptable salts thereof can also be used as an active ingredient of the medicament of the present invention. Further, any hydrate or any solvate thereof may also be used. Furthermore, for the above compound, there exist tautomers as shown in the chemical structural formula in the upper part of Section 5 of JP Patent Publication (Examined Application) No. 5-31523. Needless to say, all of these tautomers may be included as active ingredients of the medicament of the present invention.

As the salts of the above compound, acid-added salts or base-added salts can be used. For example, mineral acid salts, such as hydrochloride, sulfate, hydrobromate, or phosphate; organic acid salts, such as methane sulfonate, para-toluene sulfonate, acetate, oxalate, citrate, malate, or fumarate; metal salts, such as a sodium salt, potassium salt, or magnesium salt; ammonium salt; or organic amine salts, such as ethanol amine or 2-amino-2-methyl-1-propanol, can be used. The types of salts are not particularly limited, as long as they are physiologically acceptable.

The medicament of the present invention can be administered to any animal, including human, that suffers from motor neuron diseases, and is preferably administered to humans.

The term "treatment of motor neuron diseases" used in the present specification means not only treatment given for curing the disease, but widely means all types of treatment including treatment for delaying the progress of the disease, and treatment for alleviating and easing the symptoms of the disease.

The term "motor neuron diseases" used in the present invention has the broadest meaning, and it encompasses motor neuron disorders (motor neuropathy).

Motor neuron disease is a generic name of a disease group by which the voluntary motor nerve system is selectively impinged. Motor neuron diseases are neurologically regressive and have strong tendencies to be exacerbated, although the degree of disease progression differs depending on specific disease types. Specific examples of motor neuron diseases can include, but are not limited thereto, amyotrophic lateral sclerosis (ALS), spinal muscle atrophy (SMA), progressive bulbar palsy, primary lateral sclerosis (PLS), or arthrogryposis multiplex congenita (AMC).

Amyotrophic lateral sclerosis (ALS) begins in middle age and later, and is a cryptogenic disease mainly characterized by muscular atrophy and fasciculation. Pathologic findings include degenerated spinal anterior horn cells, degenerated medullary motor nucleus, and degenerated pyramidal tract. The initial symptoms mainly include hand weakness, dyskinesia in the digits of the hand, and fasciculation in the upper limbs, and ALS can be classified into the upper limb type, bulbar type, lower limb type and mixed type according to the onset site. With any type of the disease, muscle groups of the whole body are impinged with the progress of the symptoms.

Spinal muscle atrophy (SMA) is a post-cystic fibrosis autosomal recessive disorder (one in 6000 births), which is characterized by degenerated spinal anterior horn cells that lead to progressive numbness in symmetrical extremities and trunk associated with muscular atrophy. SMA in children is generally classified into three clinical groups based on age of onset and clinical progress. Acute Werdnig-Hoffmann disease (type I) is characterized by severe generalized muscular weakness and hypotonia at birth and within 3 months after birth. Death usually occurs within the first two years of life due to dyspnea. The remaining 2 groups are Intermediate type (type II) and Juvenile type (type III, Kugelberg-Welander disease).

Progressive bulbar palsy is caused by progressive atrophy of the motor nucleus of the medulla oblongata, and is closely associated with amyotrophic lateral sclerosis (ALS) and spinal muscular atrophy (SMA). Progressive bulbar palsy often begins in males in middle age and later, and sometimes occurs in familial forms. The disease is complicated by degeneration of upper and lower motor neurons as it progresses, and finally develops the clinical symptoms of amyotrophic lateral sclerosis (ALS).

Primary lateral sclerosis (PLS) is a variant of ALS, and is recognized as a sporadic disease in the elderly. Neuropathologically, PLS involves the degeneration of the corticospinal (pyramid) tract, which is almost normal at the brain stem level, but its contracture increases as the degeneration increases down the spinal cord. The lower limbs are most severely impinged at the initial stage.

Arthrogryposis multiplex congenita (AMC) is characterized by congenital joint contracture (1 in 3000 births), and has symptoms derived from intrauterine fetal akinesia. AMC is caused by any of oligoamnios, or various disorders relating to the central nerve system, skeletal muscle or spinal cord. Nerve degeneration and neuronophagy occurs in the anterior horn. Thus, it is assumed that neurogenic AMC may be involved in acute spinal muscular atrophy, that is, SMA Werdnig-Hoffmann disorder type I.

The route of administration of the medicament of the present invention is not particularly limited, and it can be administered orally or parenterally (for example, intravenous-, intramuscular-, hypodermic- or intradermal-injections, or inhalation).

As the medicament of the present invention, the above compound or salts thereof, which is an active ingredient, can be directly administered to a patient, and preferably, should be administered as a preparation in the form of a pharmaceutical composition containing the active ingredient and pharmacologically and pharmaceutically acceptable additives. Examples of pharmacologically and pharmaceutically acceptable additives that can be used herein include excipients, disintegrators or adjuvants for the disintegrators, binders, lubricants, coating agents, dye, diluents, bases, resolvents or solubilizers, isotonizing agents, pH modifiers, stabilizers, propellants, and adhesives. Examples of preparations, which are appropriate for oral administration, can include tablets, capsules, powders, fine granules, granules, solutions, and syrups. Examples of preparations, which are appropriate for parenteral administration, can include injections, drops or suppositories.

Examples of additives for preparations, which are appropriate for oral administration that can be used herein include: excipients such as glucose, lactose, D-mannitol, starch or crystalline cellulose; disintegrators or adjuvants for disintegrators, such as carboxymethylcellulose, starch or carboxymethylcellulose calcium; binders such as hydroxypropylcellulose, hydroxypropylmethylcellulose, polyvinylpyrrolidone, or gelatin; lubricants such as magnesium stearate, or talc; coating agents such as hydroxypropylmethylcellulose, saccharose, polyethyleneglycol, or titanium oxide; and bases such as petrolatum, liquid paraffin, polyethylene glycol, gelatin, kaolin, glycerine, purified water, or hard fat. Examples of additives for preparations that can be appropriately used for injection or drip include a resolvent or a solubilizer that can compose an aqueous injection or an injection to be dissolved before use, such as distilled water for injection, physiological saline, and propylene glycol; isotonizing agents such as glucose, sodium chloride, D-mannitol, and glycerine; and pH modifiers such as inorganic acid, organic acid, inorganic base or organic base.

The dose of the medicament of the present invention can be appropriately selected according to various conditions including types of diseases to be treated, progress of the disease or degree of the symptoms, and age and weight of patients. In general, approximately 0.01 µg/kg to 10 mg/kg, and preferably 0.1 to 100 µg/kg of the medicament per day for an adult, is administered by injection or drip. As an injection, for example, the one described in JP Patent Publication (Unexamined Application) No. 63-132833 is preferred.

Further, the above compound, which is the active ingredient of the medicament of the present invention, has been proven to be highly safe (In mouse intraabdominal administration, $LD_{50}$ is 2012 mg/kg; in rat oral administration, $LD_{50}$ is 3,500 mg/kg: Registry of Toxic Effects of Chemical Substances, 1981–1982), and to be noncarcinogenicity (National Cancer Institute Report, 89, 1978).

EXAMPLE

The present invention will hereafter be described in detail by way of Examples, but these Examples should not be taken as limiting the technical scope of the present invention.

(A) Material and Method (1) Animal

Wobbler mice (Ikeda K. et al., Ann. Neurol. vol. 34, p304, 1993; Mitsumoto H. et al., Ann. Neurol. vol. 36, pp142 to 148, 1994; Mitsumoto H. et al., Science, vol. 265, pp1107 to 1110, 1994) were used.

(2) Administration of Drug

At 3 to 4 weeks old, with the development of the symptom of body tremors, Wobbler mice were diagnosed with the onset of the disease. Immediately after being diagnosed to have the beginnings of the disease, the mice were orally administered with the drug of the present invention (3-methyl-1-phenyl-2-pirazoline-5-on; also referred to as MCI-186 in the drawings) (10 mg/kg), and the mice of a control group were administered with vehicles, by a blind test continually for 4 weeks. The administration of the drug was completed at 7 to 8 weeks old after birth, and the test was conducted with n=10 for each test group.

(3) Symptomatological Evaluation

The degree of forelimb deformity was classified into four grades: 1 (paw atrophy), 2 (curled digits), 3 (curled wrists), and 4 (forelimb flexion to chest), and then evaluated. The progress from 1 to 4 means that the symptom became worse.

The grip strength of the forelimb was measured (Ikeda et al., Neuromusc. Disord., 5, (1995), 383–390; K. Ikeda et al., J. Neurol. Sci., 160, (1998) 9–15; K. Ikeda et al., Neurosci. Lett., 250 (1998) 9–12; K. Ikeda et al., Muscle Nerve, 18 (1995) 1344–1347; K. Ikeda et al., Neurol. Res., 17 (1995) 445–448; K. Ikeda et al., Ann. Neurol., 37 (1995) 505–511; K. Ikeda et al., Brain Res., 726 (1996) 91–97; H. Mitsumoto et al., Ann. Neurol., 36 (1994) 142–148; and H. Mitsumoto et al., Science, 265 (1994) 1107–1110). These evaluations were performed every week from the start (before administration) to the end of drug administration.

(4) Morphological Studies on Right Brachial Biceps Muscle

After the end of drug administration, Wobbler mice (n=10 per group) were ether anesthetized, and then the right brachial biceps muscles were excised under dissecting microscope. The excised biceps muscles were correctly measured, and then frozen. Serial sections (10 µm) were prepared, and then stained with ATPase or NADH. Mean diameter of the muscle fibers was measured as described in previous reports (Ikeda et al., Neuromusc. Disord., 5 (1995) 383–390; K. Ikeda et al., J. Neurol. Sci., 160 (1998) 9–15; K. Ikeda et al., Neurosci. Lett., 250 (1998) 9–12; K. Ikeda et al., Muscle Nerve, 18 (1995) 1344–1347; K. Ikeda et al., Neurol. Res., 17 (1995) 445–448; K. Ikeda et al., Ann. Neurol., 37 (1995) 505–511; K. Ikeda et al., Brain Res., 726 (1996) 91–97; and H. Mitsumoto et al., Ann. Neurol., 36 (1994) 142–148).

(5) Number of Spinal Motor Neurons

Wobbler mice (n=10 per group) that had been used for morphological study on the right brachial biceps muscles were perfused via an intracardiac catheter with phosphate buffered saline, and then 4% paraformaldehyde/1% glutaraldehyde/0.1 M sodium phosphate buffer (pH 7.4). The vertebral arches were excised, and then the cervical spinal cords were removed under dissecting microscope. Cervical spinal cord $C_{5-6}$ levels to stimulate the biceps were excised for analysis of motor neurons, and then embedded with paraffin. An 8 μm transverse section was continuously cut, and stained with cresyl violet, and then the number of large spinal motor neurons was measured as described in previous reports (Ikeda et al., Neuromusc. Disord., 5 (1995) 383–390; K. Ikeda et al., J. Neurol. Sci., 160 (1998) 9–15; K. Ikeda et al., Neurosci. Lett., 250 (1998) 9–12; K. Ikeda et al., Muscle Nerve, 18 (1995) 1344–1347; K. Ikeda et al., Neurol. Res., 17 (1995) 445–448; K. Ikeda et al., Ann. Neurol., 37 (1995) 505–511; and K. Ikeda et al., Brain Res., 726 (1996) 91–97).

(6) Statistical Analysis

The scale of the degree of forelimb deformity was analyzed by the non-parametric Wilcoxon signed rank-sum test. Muscle strength, weight of biceps muscle, mean diameter of muscle fibers and number of motor neurons were statistically analyzed by unpaired Student's t-test. In all tests, the significance level of 5% was set for both sides.

(B) Result (1) Symptomatological Evaluation

FIG. 1 shows the evaluation results when the degree of forelimb deformity was classified into Grades 1 to 4. Evaluation at the baseline (3 to 4 week-old after birth) did not differ between each group. Forelimb deformity became progressively worse among the mice of the control group, but the progress of muscle deformity was delayed by the administration of the medicament of the present invention (FIG. 1).

Figure 2:
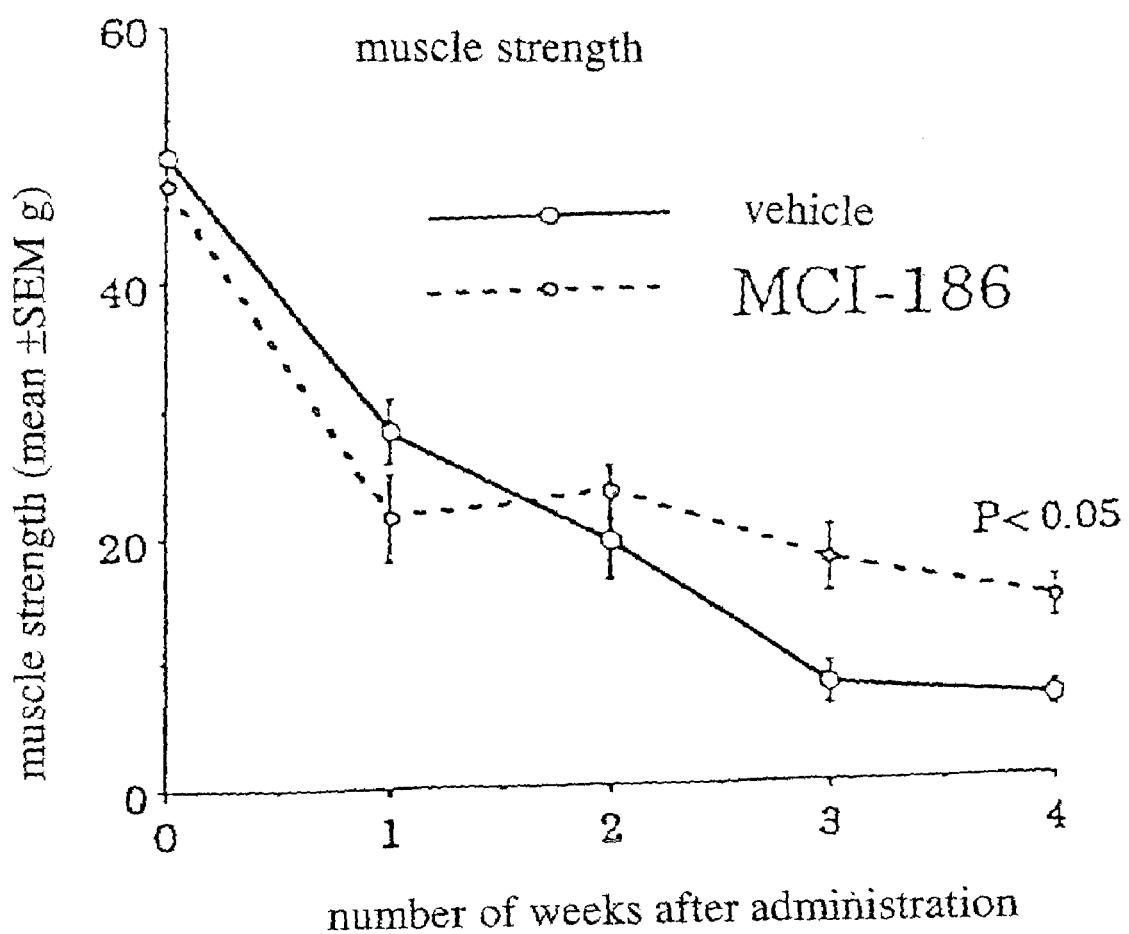
FIG. 2 shows the results of measurements of forelimb muscle strength.

FIG. 2 shows the results of measuring muscle strength of the forelimb. The muscle strength in the control group gradually decreased, but the decrease in muscle strength was delayed by the administration of the medicament of the present invention (FIG. 2).

(2) Weight of Right Brachial Biceps Muscle and Morphological Study on Muscle

Figure 3:
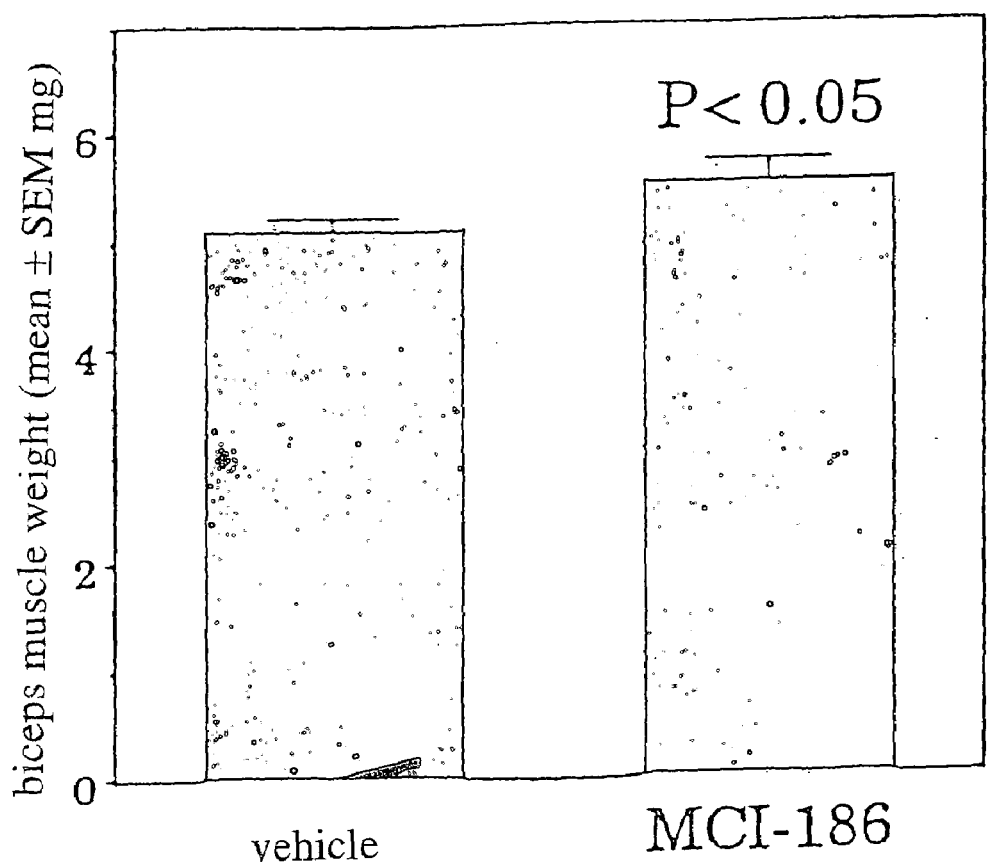
FIG. 3 shows the results of measurements of the right brachial biceps muscle weight.

FIG. 3 shows the results of measuring weights of the right brachial biceps muscles. The weight of the biceps significantly increased by the treatment with the medicament of the present invention, as compared to the control group (FIG. 3).

The mean diameter of muscle fibers significantly increased in the group treated with the medicament of the present invention (mean±SEM: 20.3±0.8 μm, P<0.01), as compared to the control group (mean±SEM: 16.8±0.6 μm, P<0.01).

(3) Number of Spinal Motor Neurons

Figure 4:
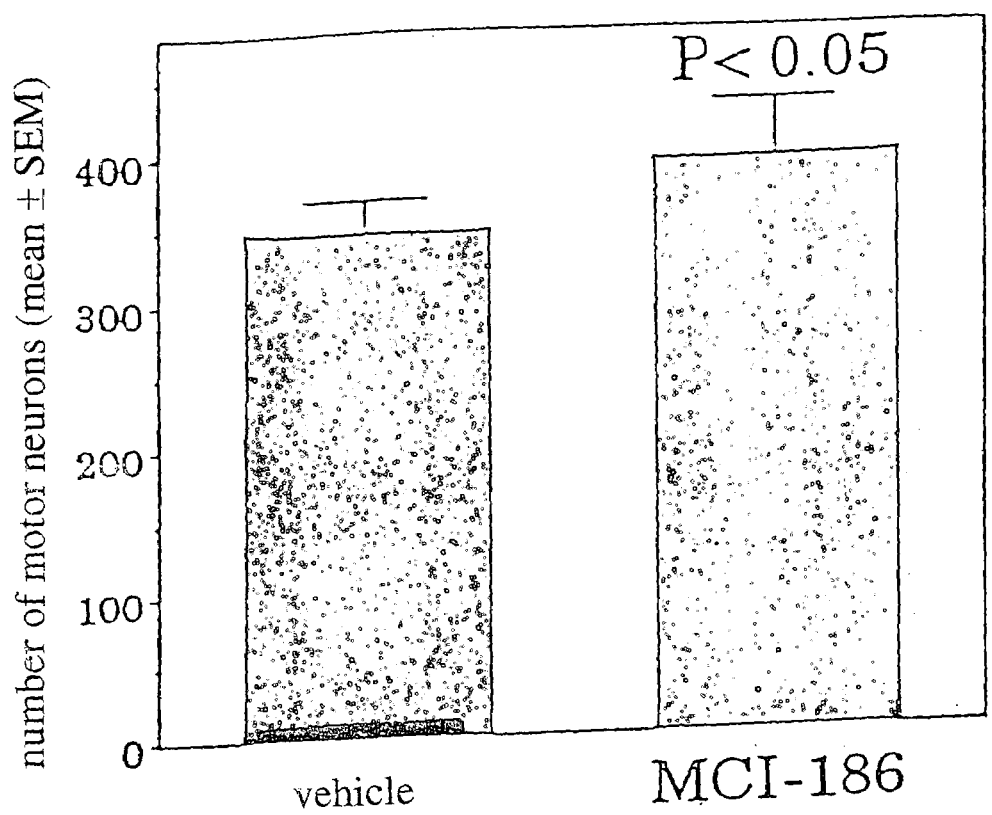
FIG. 4 shows the results of measurements of the number of spinal motor neurons.

FIG. 4 shows the results of measuring the number of motor neurons. As compared to the control group, the number of motor neurons increased in the group treated with the medicament of the present invention (FIG. 4).

(4) Conclusion

Wobbler mice are motor neuron disease model animals that develop an autosomal recessive inheritance pattern. In these animals, the disease begins with body tremors at 3 to 4 weeks after birth, and muscle weakness and muscle deformity mainly in the forelimb rapidly progress 7 to 8 weeks after birth. Thereafter, the neuromuscular symptoms slowly progress and the life span is approximately 1 to 1.5 years. Neuromuscular pathological features of the mice are vacuolar degeneration of motor neurons centering on the cervical spinal cord, axonal degeneration in motor nerves, and neurogenic changes in the skeletal muscle (H. Mitsumoto et al., Brain, 105 (1982) 811–834). Therefore, evaluation of the neuroprotective action of the therapeutic agent in the mice at 3 to 4-week-old to 7 to 8-week-old is useful in evaluating the effect of the therapeutic agent against motor neuron diseases.

In this Example, it was proven that in Wobbler mice treated with 3-methyl-1-phenyl-2-pirazoline-5-on, forelimb deformity and muscle weakness were alleviated, and the brachial biceps muscle increased in weight. Thus, the medicament of the present invention is useful as a therapeutic agent against motor neuron diseases.

INDUSTRIAL APPLICABILITY

The medicament of the present invention which comprises 3-methyl-1-phenyl-2-pirazoline-5-on or physiologically acceptable salts thereof as an active ingredient, is useful as a therapeutic agent against motor neuron diseases. Further, the medicament of the present invention is advantageous in that migration to the brain is relatively good, because a low molecular compound is used as an active ingredient.

What is claimed is:

1. A method for treating motor neuron diseases consisting essentially of administering an effective amount of 3-methyl-1-phenyl-2-pyrazoline-5-one or a physiologically acceptable salt thereof to a patient.

2. The treatment method according to claim 1 wherein the progress of motor neuron diseases is delayed.

3. The treatment method according to claim 1 wherein the motor neuron disease is amyotrophic lateral sclerosis (ALS), spinal muscle atrophy (SMA), progressive bulbar palsy, or primary lateral sclerosis (PLS).

4. The treatment method according to claim 1 wherein the motor neuron disease is amyotrophic lateral sclerosis (ALS).

5. A method for enhancing motor neurons consisting essentially of administering an effective amount of 3-methyl-1-phenyl-2-pyrazoline-5-one or a physiologically acceptable salt thereof to a patient.

* * * * *